United States Patent [19]
Dubroff

[11] Patent Number: 5,188,590
[45] Date of Patent: Feb. 23, 1993

[54] BUFFER-CONTAINING DEVICES FOR PREVENTING CLOUDING OF POSTERIOR CAPSULE AFTER EXTRACAPSULAR CATARACT EYE SURGERY AND METHOD OF PERFORMING CATARACT SURGERY

[76] Inventor: Seymour Dubroff, 3806 Thornapple St., Chevy Chase, Md. 20815

[21] Appl. No.: 674,895

[22] Filed: Mar. 26, 1991

Related U.S. Application Data

[63] Continuation-in-part of Ser. No. 483,719, Feb. 12, 1990, Pat. No. 5,080,647, which is a continuation-in-part of Ser. No. 173,625, Mar. 25, 1988, Pat. No. 4,909,784.

[51] Int. Cl.$^5$ ............................................. A61B 17/20
[52] U.S. Cl. ...................................... 604/22; 604/27; 604/49
[58] Field of Search ................. 604/22, 27, 28, 38, 604/49, 289, 290; 606/107

[56] References Cited

U.S. PATENT DOCUMENTS

| | | | |
|---|---|---|---|
| 4,191,176 | 3/1980 | Spina et al. | 604/22 |
| 4,515,794 | 5/1985 | Emery et al. | 514/249 |
| 4,650,461 | 3/1987 | Woods | 604/28 |
| 4,871,350 | 10/1989 | Lam et al. | 604/49 |
| 4,918,165 | 4/1990 | Soll et al. | 530/391 |
| 4,965,253 | 10/1990 | Goldberg et al. | 514/54 |
| 4,966,577 | 10/1990 | Crosson et al. | 604/20 |

Primary Examiner—Stephen E. Pellegrino
Assistant Examiner—Michael Rafa

[57] ABSTRACT

The present invention relates to devices for killing undifferentiated epithelial cells during cataract surgery on an eye to prevent posterior capsule clouding after the surgery and to a method for performing cataract surgery on an eye including injecting a cell-killing substance between the anterior capsule and the natural lens prior to removing the natural lens from the eye. The cell-killing substance is preferably an acid or base adjusted, aqueous, buffer-containing a solution having a pH in the range between about 1.0 to below 6.5 or about above 7.5 to 14.0 or a buffer-containing hypotonic solution having a salinity less than 0.06%. The devices of the present invention optionally incorporate a viscoelastic material, a dye or a mixture thereof, in combination with the cell-killing substance.

41 Claims, 1 Drawing Sheet

BUFFER-CONTAINING DEVICES FOR PREVENTING CLOUDING OF POSTERIOR CAPSULE AFTER EXTRACAPSULAR CATARACT EYE SURGERY AND METHOD OF PERFORMING CATARACT SURGERY

RELATED APPLICATIONS

The present application is a continuation-in-part of Ser. No. 07/483,719, filed Feb. 12, 1990 now U.S. Pat. No. 5,080,647 which is a continuation-in-part of 07/173,625, filed Mar. 25, 1988 now U.S. Pat. No. 4,909,784.

BACKGROUND OF THE INVENTION

1. Field of the Invention

The present invention pertains to cataract surgery and, more particularly, to the prevention of clouding of the posterior capsule after extracapsular cataract extraction.

2. Discussion of the Prior Art

Clouding of the posterior capsule after extracapsular cataract extraction, with or without the implant of an intraocular lens, has been a principal, later occurring, complication of such extracapsular cataract surgery. During cataract surgery, it is preferable to extract the natural lens while leaving the posterior portion of the lens capsule intact in front of the vitreous cavity of the eye to provide a barrier to prevent anterior movement or loss of the vitreous which fills the cavity and to also provide a support for an intraocular lens implanted in the posterior chamber. If the natural lens is removed intact with the capsule, referred to as intracapsular cataract extraction, the vitreous can move through the pupil causing vitreous loss and increasing the chances of complications, such as glaucoma, corneal opacity, displacement of an intraocular lens, retinal hemorrhage, holes, breaks and detachment, and cystoid macula edema.

In many cases after extracapsular cataract extraction, with or without the implant of an intraocular lens, the posterior capsule becomes opacified or clouded due to migration of proliferating undifferentiated epithelial cells into the optical zone which, clustered, form Elschnig's pearls. Along with Elschnig's pearls, visual acuity is also reduced by invading fibroblasts through metaplasia developing into myoepithelial fibers, lens fibers, collagen, fibrosis and Sommering rings. This opacification or clouding of the posterior capsule, referred to as secondary cataract, occurs in a large percentage of extracapsular cataract extractions and is a primary cause of post operative complications.

One procedure to remove secondary cataracts is discission using a needle or scissors to punch or cut a hole in the posterior capsule. Another procedure includes the use of a YAG laser focused through the pupil to open the posterior capsule. Such procedures, referred to as posterior capsulotomy, remove the opacification to improve sight; however, they also create the adverse effects discussed above with respect to intracapsular cataract extraction due to the removal of the barrier to vitreous movement.

Other attempts to prevent clouding of the posterior capsule include constructing intraocular lenses to produce barriers to movement of the undifferentiated epithelial cells from the equator of the posterior capsule toward the optical zone; however, such intraocular lenses have been difficult to implant in the posterior capsule and have not created effective barriers to prevent clouding.

Still another attempt to prevent proliferation of lens epithelial cells after extracapsular cataract extraction is shown in U.S. Pat. No. 4,432,751, to Emery et al, which instills monoclonal antibodies specific to lens epithelial cells into the anterior chamber to cause lysis or other damage to the lens epithelial cells and prevent the cells from multiplying and covering the posterior lens capsule.

Accordingly, there is a great need for a manner in which to prevent opacification of the posterior capsule, particularly in view of the great number of cataract surgeries performed each year and the substantial likelihood of most individuals having cataract surgery due to the natural forming of cataracts in the natural lens with aging. As noted above, the preferable procedure for cataract surgery is extracapsular cataract extraction; and, thus, much effort has been directed toward overcoming the late capsule clouding complication associated with such cataract surgery.

SUMMARY OF THE INVENTION

Accordingly, it is a primary object of the present invention to prevent clouding of the posterior capsule after extracapsular cataract extraction without requiring removal, puncturing or discission of the posterior capsule.

A further object of the present invention is to prevent clouding of the posterior capsule after extracapsular cataract extraction by killing remaining undifferentiated epithelial cells by either osmotic cellular destruction in a hypotonic environment and/or lysis by destructive pH alteration.

Another object of the present invention is to provide a method of performing cataract surgery on an eye to prevent capsule clouding after the surgery by injecting a cell-killing substance between the capsule and the natural lens and thereafter removing the natural lens from the eye.

Yet another object of the present invention is to provide a cell-killing substance of a buffered hypotonic (hypo-osmotic) solution or a buffered pH adjusted solution having a pH either below 6.5 or above 7.5 for injection between the capsule and the natural lens of an eye prior to removal of the natural lens to kill the undifferentiated epithelial cells by osmotic cellular destruction and/or by destructive pH alteration.

It is still another object of the present invention to employ a buffer in hypotonic solutions or pH adjusted solutions to increase the effectiveness of these solutions in killing undifferentiated epithelial cells by osmotic cellular destruction and/or by destructive pH alteration.

It is still another object of the present invention to incorporate a buffer into a cell-killing substance to assure contact of the cell-killing substance with all undifferentiated epithelial cells.

It is still another object of the present invention to provide a method and composition to break down covering cortical debris to expose epithelial cells to the effects of the buffer-containing cell-killing substance during ophthalmic surgery.

Yet an additional object of the present invention is to place a viscoelastic material in the anterior chamber of an eye prior to injecting a cell-killing substance between the capsule and the natural lens such that the viscoelastic material prevents any cell-killing substance escaping from the capsule opening from reaching the corneal endothelium.

The present invention is characterized by a device in the form of a solution for administration between the anterior capsule and the lens during cataract surgery including a buffer-containing, cell-killing substance having improved properties to kill undifferentiated lens epithelial cells by osmolysis and/or destructive pH alteration, and optionally contains a viscoelastic material, a dye or both.

The present invention is further characterized in a method of performing cataract surgery on an eye to prevent capsule clouding after the surgery comprising the steps of: (1) injecting the cell-killing substance between the capsule and the natural lens, the substance having properties to kill undifferentiated epithelial cells; (2) maintaining the cell-killing substance in contact with the undifferentiated epithelial cells for a sufficient period of time to kill these cells by osmotic cellular destruction or destructive pH alteration; and (3) removing the natural lens from the eye.

Some of the advantages of the present invention over prior art methods of preventing or eliminating capsule clouding are that the device and method of the present invention can be utilized along with the procedures of normal cataract surgery requiring only a single additional procedure, no difficult or complex surgical procedures are required, safety is assured by the use of viscoelastic materials and the nature of the device assures the killing or destruction of all undifferentiated epithelial cells.

Other objects and advantages of the present invention will become apparent from the following description of the preferred embodiment taken in conjunction with the accompanying drawings.

DESCRIPTION OF THE PREFERRED EMBODIMENT

Figure 1:
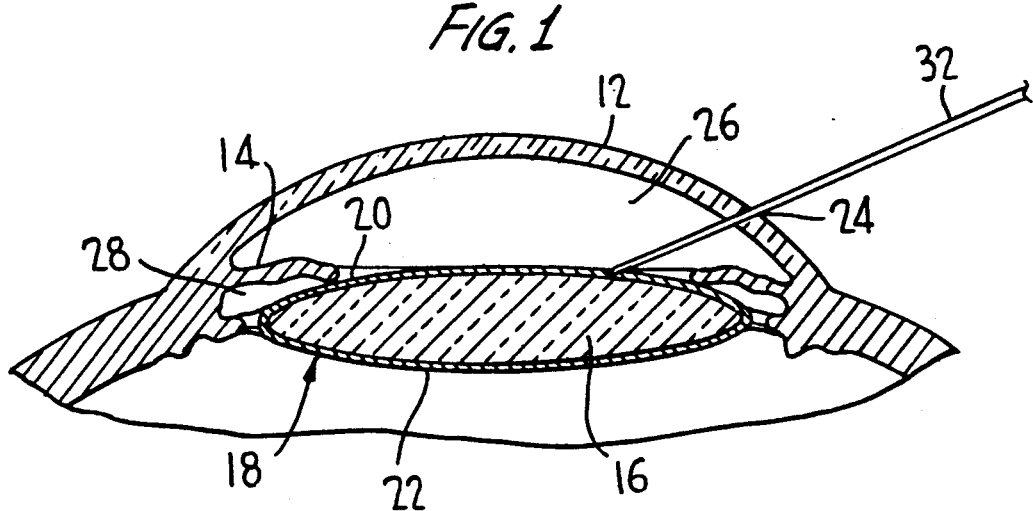
FIG. 1 is a cross-section of an eye illustrating injection of a cell-killing substance in accordance with the present invention.
Figure 2:
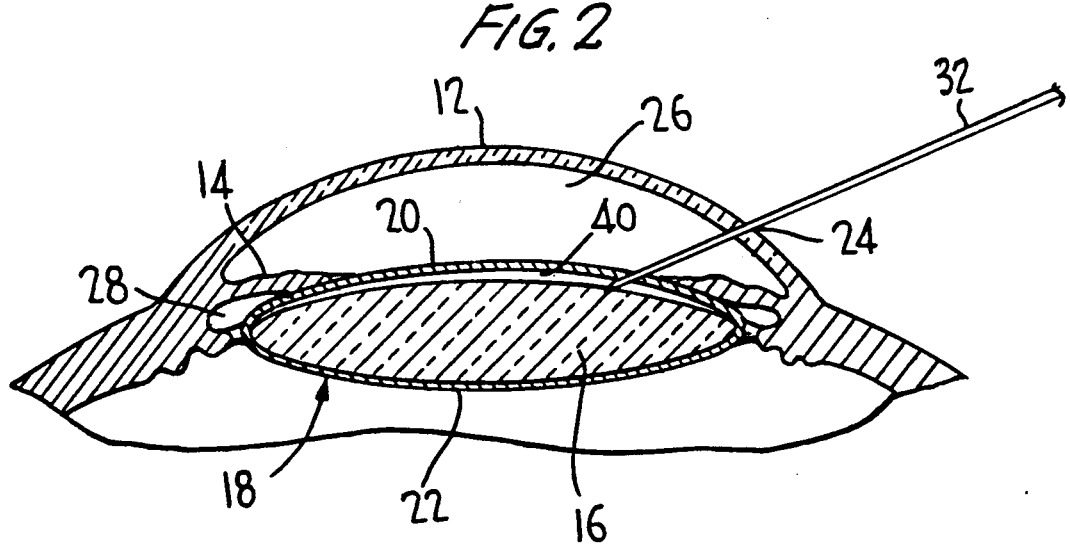
FIG. 2 is a cross-section of an eye after injection of the cell-killing substance in accordance with the present invention.

The present invention will be explained with respect to FIGS. 1 and 2 which illustrate an eye including a cornea 12, an iris 14, a natural lens 16 and a capsule 18 surrounding the lens formed of an anterior capsule segment 20 and a posterior capsule segment 22. In conventional extracapsular cataract surgery, an incision 24 is made in the cornea, and an anterior capsulotomy is performed to remove a portion of the anterior segment 20 of the capsule. Thereafter, the natural lens 16 is removed; and, if desired, an intraocular lens can be positioned in either the anterior chamber 26, defined as the region between the cornea and the iris, or the posterior chamber 28, defined as the region behind the iris, posterior chamber intraocular lenses being positioned normally in the posterior capsule 22 or in the sulcus.

In accordance with the present invention, after the incision 24 is made, a syringe is inserted therethrough having a hollow hypodermic needle 32. The surgeon punctures the anterior segment 20 of the capsule 18 with the needle 32; and, once the needle 32 is so positioned, the syringe is operated to force a cell-killing substance between the capsule 18 and the lens 16 to form a fluid pocket 40, the substance at least completely surrounding the anterior surface of the lens to completely contact the anterior capsule segment 20. The cell-killing substance is maintained in contact with the undifferentiated epithelial cells for a period sufficient to kill all of the undifferentiated epithelial cells. A particularly effective syringe for introducing the cell-killing substance is shown and described in U.S. Pat. No. 4,909,784 and includes an aspirating tube having an open distal end disposed adjacent the capsule to evacuate any cell-killing substance escaping from the capsule. Furthermore, to ensure that the cell-killing substance does not come into contact with the cornea or other eye tissues, the anterior chamber 26 is filled with a viscoelastic material, such as VISCOAT produced by Alcon Laboratories, Inc.

The cell killing substances of the present invention include buffer-containing hypotonic solutions or buffer-containing pH adjusted solutions. These cell-killing substances destroy the undifferentiated epithelial cells by osmolysis and/or by destructive pH alteration. Upon contacting the undifferentiated epithelial cells with a hypotonic solution cell-killing substance, the cells continuously absorb the cell-killing substance by osmosis until the cells are destroyed by bursting or exploding within approximately thirty seconds. Additionally, the undifferentiated epithelial cells can undergo a destructive pH change by contacting the cells with a pH adjusted solution cell-killing substance thereby killing the cells within approximately a minute by altering the normal chemical reactions required for metabolic activity essential for the life of the cell. Thus, the cell-killing substance should be maintained in contact with the epithelial cells for a period of time sufficient to complete destruction of the cells by osmolysis or by altered pH lysis.

The hypotonic solutions and the pH adjusted solutions used as epithelial cell-killing substances or solutions each contain a buffer system. The buffer systems used for the purpose of the instant invention are buffer systems capable of stabilizing and maintaining the pH of these hypotonic or pH adjusted solutions at any pH, but preferably in the pH range from about 4.5 to 9.5. The incorporation of a buffer system into any of these solutions increases the epithelial cell-killing effectiveness of these solutions in comparison with comparable solutions not containing buffer systems. Based upon this increased effectiveness it is believed that the incorporation of buffer systems into these hypotonic or pH altering solutions assists in promoting separation of the anterior segment 20 of the capsule 18 and the lens 16 thereby permitting the cell-killing substance to contact and kill essentially all of the undifferentiated epithelial cells located between the capsule and the lens, it being noted that the area shown between the anterior capsule segment and the lens is, in fact, only a potential space naturally resisting separation.

Typical buffering systems for use in the present invention include any conventional ophthalmically acceptable buffer including but not limited to: sodium phosphate, sodium dihydrogenphosphate, disodium hydrogenphosphate, sodium biphosphate, sodium acetate, boric acid, sodium hydrogen carbonate, potassium acid phosphate and the like. Typical buffers or buffer systems include phosphate salt buffer systems, citric acid systems, boric acid systems, sodium borate systems, acetate salt systems, bicarbonate salt systems, trisamine salt systems and the like. The preferred buffer or buffer system for use in the present solutions is a combination of sodium dihydrogenphosphate (sodium phosphate monobasic) and disodium hydrogenphosphate (sodium phosphate dibasic). Typical buffers are employed in amounts from 0.05 to 5.0 weight percent of the completed solution, preferably from 0.5 to 3.0 weight percent of the completed solution.

A preferred buffer system for use in the present invention contains 0.25 to 0.50 grams of sodium phosphate dibasic and 0.50 to 1.00 grams of sodium phosphate monobasic per 100 cc of the completed solution.

The buffer system is typically utilized to buffer solutions between a pH range from 5.5 to 8.5, preferably 6.5 to 7.5. If a hypotonic or pH altering solution is desired having a pH within or outside of this range, then a sufficient amount of ophthalmically acceptable acid or base is added to the solution to achieve the desired pH level by overloading the buffering capacity of the solution. While buffer systems are normally employed to maintain or stabilize a solution at a desired pH range, the use of a buffer system in the solutions in the present invention further serves to increase the epithelial cell-killing effectiveness of the hypotonic and pH adjusted solutions.

Hypotonic (hypo osmotic) solutions are defined herein as any solution having an osmotic pressure lower than the pressure naturally existing in the undifferentiated epithelial cells. Thus, any solution providing an osmotic pressure below normal saline solution can be employed in accordance with the present invention. Organic hypotonic solutions can be utilized including, but not limited to, alcohols, ketones, ethers or aldehydes.

Preferred hypotonic solutions include buffer-containing distilled water or water having a salinity less than 0.9%. Preferably, the buffer-containing hypotonic solution injected as a cell-killing substance has a salinity of from 0 to 0.6%, it being found that salinity percentages of from 0 to 0.3% are highly effective. Suitable salts such as NaCl or other pharmaceutically acceptable salts are utilized to effect the desired percentage of salinity.

In other terms, the present hypotonic solutions possess an osmolarity of less than 270 milliosmoles/kg of solute, preferably less than 180 mOSm, most preferably less than 90 mOSm. The hypotonic solutions of the present invention can possess a pH in any range that can be safely used in the surgical ocular environment. The hypotonic solutions can have a pH ranging from 1 to 14 and have a preferred pH range from about 4.5 to about 9.0, most preferably about 5.8 to about 8.4.

The buffer-containing pH adjusted solutions of the present invention have either a pH in the acidic pH range between approximately 1.0 to below 6.5 or in the basic pH range between approximately above 7.5 to 14.0. The preferred pH adjusted solutions used as cell-killing substances possess a pH in either of the following two ranges: $3.5 \leq pH \leq 6.5$ or $7.5 \leq pH \leq 10.5$. More preferably the pH adjusted solutions posess a pH ranging either between 5.8 to 6.2 or between 8.0 to 8.4, while the most preferable pH adjusted solutions are pH adjusted aqueous solution having a pH of either approximately 6.0 or 8.2. While it is preferable that the buffer-containing pH adjusted solutions be hypotonic, non-hypotonic solutions can be employed to kill the epithelial cells by destructive pH alteration.

The pH adjusted solutions used as pH altering cell-killing substances are organic or inorganic, aqueous preferably and are produced by sequentially adding a buffer and then either basic or acid components to organic or inorganic diluents. The acidic pH adjusted solutions are produced by adding a buffer and then an appropriate amount of HCl, preferably, or other ophthalmically acceptable acids to a diluent such as water. The basic pH adjusted solutions are produced by adding a buffer and then an appropriate amount of NaOH, preferably, or other ophthalmically acceptable bases to a diluent such as water. Other ophthalmically acceptable acids for use in the present invention to prepare the pH adjusted solutions include but are not limited to: mineral acids and organic acids such as $H_2SO_4$, $HNO_3$, $H_3PO_4$, acetic, proprionic, oxalic, maleic, benzoic acids and the like. Other ophthalmically acceptable bases include but are not limited to: alkali or alkaline earth hydroxides, carbonates or bicarbonates or the like, preferably potassium hydroxide.

The pH of the buffer-containing hypotonic solutions for use in the present invention is suitably adjusted to enhance the ability of the solution to destroy undifferentiated epithelial cells. The pH of the buffer-containing hypotonic solution is controlled by the appropriate addition of acids or bases utilized to adjust the pH in the pH adjusted solutions. These hypotonic solutions formed in this manner can have a pH ranging between 1 and 14. The pH adjusted hypotonic solutions destroy undifferentiated epithelial cells by both osmolysis and by destructive pH alteration to assure that all cells are destroyed.

As noted above, the pocket 40 is essentially a "potential" space in that the capsule is contracted tightly around the lens. Since it is preferable to contact all undifferentiated epithelial cells with the cell-killing substance, the potential space must be expanded in all areas between the lens and the anterior capsule segment to form pocket 40. The injected cell-killing substance may completely surround the lens 16 between both the anterior capsule 20 and the posterior capsule 22; however, as illustrated in FIG. 2, it is important only that a sufficient amount of solution be injected to form a fluid pocket 40 allowing the cell-killing substance to contact all portions of the anterior capsule segment since undifferentiated epithelial cells only habitat in the lens capsule 18 between the anterior capsule 20 and the lens 16. Upon the initial separation of the lens 16 and the anterior capsule 20 caused by the injection, cortical fibers forming pockets of cortical debris remain attached to the anterior capsule. The cortical debris covers a monolayer of undifferentiated epithelial cells on the anterior capsule surface and acts as a barrier to potential attack on such cells. Unexpectedly, it is believed that the addition of a buffer system to the cell-killing substances improves the ability of the injected cell-killing substances to break down this cortical debris barrier and to kill all undifferentiated epithelial cells present between the lens 16 and the anterior capsule 20.

It has been found that, optionally, the use of a viscoelastic material in admixture with the cell-killing substance, preferably premixed prior to injection, facilitates the even flow of the admixture to form fluid pocket 40 and assures that all areas of the anterior surface of lens 16 and the posterior surface of anterior capsule segment 20 come into contact with the cell-killing substance. The admixture of the viscoelastic material with the cell-killing substance facilitates the spread of the admixture onto the surface of the outer periphery of lens 16. Furthermore, the use of the viscoelastic material increases the contact time between the cell-killing substance and the undifferentiated epithelial cells through retention of the cell-killing substance against the epithelial cells by the viscoelastic material.

Preferred viscoelastic materials for use in admixture with the cell-killing substances of the instant invention include, but are not limited to, HEALON, VISCOAT, ORCULON, methylcellulose, methyl hyaluronate, polyacrylamide and polymethacrylamide. The viscoelastic material is preferably utilized in amounts ranging from 0.5 to 5.0%, preferably 1 to 3% by weight of the cell-killing substance injected into fluid pocket 40.

As pointed out above, it is important to contact all undifferentiated epithelial cells with the cell-killing substance; however, it is extremely difficult for the surgeon to visually determine that the cell-killing substance has completely filled the pocket and expanded all portions of the anterior capsule segment. Accordingly, a dye is admixed with the cell-killing substance prior to or after injection of the cell-killing substance between the inner surface of the anterior capsule 20 and the lens 16. The use of such a dye provides visually recognizable color to the injected solution so that a surgeon can visually determine the extent of the flow of the injected solution between the anterior capsule 20 and the lens 16. The surgeon can thus visually confirm that the cell-killing substance has completely filled the capsule space forming fluid pocket 40 between the anterior capsule 20 and the lens 16 so that all of the anterior capsule 20 comes in fluid contact with the cell-killing substance.

Preferred dyes for use in combination with the cell-killing substance of the present invention include, but are not limited to, methylene blue and triptolene blue. It has been determined that blue, purple and green dyes provide the best contrast for visualization during insertion of the cell-killing substance; however, any dye providing sufficient contrast to show the extent of the area of coverage of the cell-killing substance between the anterior capsule 20 and the lens 16 can be utilized. When utilized, the aforementioned preferred colors also provide the best contrast with cataracts which appear to be amber in color.

The dyes should be utilized in amounts to effectively provide color to the cell-killing substance upon visual examination. It is preferable to incorporate a dye in extreme dilution to provide a visually apparent amount, preferably from 0.1 to 10 parts per million of the cell-killing substance.

The cell-killing substances may be administered alone, in combination with a dye or a viscoelastic material, or in combination with both a dye and a viscoelastic material in accordance with the present invention. Any combination of the aforementioned substances, namely the buffer-containing cell-killing substance alone or together with the dye and/or the viscoelastic material, is preferably administered by injection in an amount of less than 2.0 cc, most preferably less than 1.5 cc, between the lens 16 and the anterior segment 20 of the capsule 18 such that there is minimal opportunity for the substance to escape from the capsule while still providing full fluid contact of the injected cell-killing substance solution between the inner anterior capsule surface and the lens surface, preferably at least 0.5 cc.

In use, a syringe is filled with the buffer-containing cell-killing substance, which may be optionally admixed with a dye and/or a viscoelastic material; and, as a piston is forced into a chamber in the syringe, the cell-killing substance or mixture thereof is forced through needle 32 between the anterior capsule 20 and the natural lens 16 with sufficient pressure to surround the lens and kill epithelial cells therein by osmotic pressure.

Any cell-killing substance inadvertently escaping from the capsule through the puncture is constrained to move along the needle and through incision 24 due to the viscoelastic in the anterior chamber 26 or can be collected by an aspirating tube. Accordingly, the cell-killing substance is prevented from contact with any eye tissue.

In view of the above, it will be appreciated that the method of preventing capsule clouding according to the present invention is extremely simple and efficacious in that the capsule is used to confine the cell-killing substance but is not a living cell and, therefore, is not affected by the cell-killing substance.

Inasmuch as the present invention is subject to many variations and modifications in detail, it is intended that all subject matter discussed above or shown in the accompanying drawings be interpreted as illustrative and not in a limiting sense.

What is claimed is:

1. A method of performing cataract surgery on an eye to prevent capsule clouding after the surgery comprising the steps of injecting a buffer-containing hypotonic solution between an anterior capsule and a natural lens, said solution having properties to kill undifferentiated epithelial cells.

2. The method of claim 1 additionally comprising the step of mixing a dye with said buffer containing hypotonic solution.

3. The method of claim 1 additionally comprising the step of mixing a viscoelastic material with said buffer-containing hypotonic solution.

4. The method of claim 1 additionally comprising the step of adjusting the pH of the buffer-containing hypotonic solution to a pH in the range from 1.0 to 14.0.

5. The method of claim 4 additionally comprising the step of mixing a dye with said buffer-containing hypotonic solution.

6. The method of claim 4 additionally comprising the step of mixing a viscoelastic material with said buffer-containing hypotonic solution.

7. The method of claim 1 additionally comprising the step of adjusting the pH of the buffer-containing hypotonic solution to a pH in the range from between 4.5 to 9.5.

8. A method of performing cataract surgery on an eye to prevent capsule clouding after the surgery comprising the step of injecting a solution comprising a buffer-containing cell-killing substance between the capsule and the natural lens, the substance having a pH ranging from below 6.5 to 1.0 or from above 7.5 to 14.0 and having properties to kill undifferentiated epithelial cells.

9. The method of performing cataract surgery as recited in claim 8 wherein the cell killing substance comprises a combination of water, a buffer and an acid or a combination of water, a buffer and a base whereby the epithelial cells are killed.

10. The method of performing cataract surgery as recited in claim 8 wherein said injecting step includes forcing the substance between the capsule and the natural lens under pressure and further comprising the step of aspirating from the eye any of the substance escaping from the capsule.

11. The method of performing cataract surgery as recited in claim 8 wherein the substance comprises a solution of water, a buffer and a base, said solution having a pH in a range from approximately 8.0 to about 8.4.

12. The method of performing cataract surgery as recited in claim 8 wherein the substance comprises a solution of water, a buffer and an acid, said solution having a pH in a range from between approximately 5.8 to 6.2.

13. The method as recited in claim 8 additionally comprising the steps of mixing a viscoelastic material with said cell-killing substance to form said solution prior to injecting said solution.

14. The method as recited in claim 13 additionally comprising the step of mixing a dye with said solution.

15. The method as recited in claim 8 additionally comprising the step of mixing a dye with said solution.

16. The method of performing cataract surgery as recited in claim 14 and further comprising the step of, prior to said injecting step, placing a viscoelastic material in the anterior chamber of the eye whereby any of the substance escaping from the capsule is prevented from reaching the corneal endothelium.

17. The method of performing cataract surgery as recited in claim 8 and further comprising the step of, prior to said injecting step, placing a viscoelastic material in the anterior chamber of the eye whereby any of the substance escaping from the capsule is prevented from reaching the corneal endothelium.

18. A method of performing cataract surgery on the eye to prevent capsule clouding after the surgery comprising the step of injecting a solution comprising a mixture of a cell-killing substance containing a buffer and a viscoelastic material between the capsule and the natural lens, said cell-killing substance having properties to kill undifferentiated epithelial cells.

19. The method as recited in claim 18 additionally comprising the step of mixing a dye with said solution.

20. A method of performing cataract surgery on the eye to prevent capsule clouding after the surgery comprising injecting a cell-killing substance containing a buffer and a dye between the capsule and the natural lens, the substance having properties to kill undifferentiated epithelial cells.

21. A method of performing cataract surgery on the eye to prevent capsule clouding after the surgery comprising the steps of injecting a solution comprising a buffer-containing, cell-killing substance in an amount of less than 2.0 cc between the anterior capsule and the natural lens, said cell-killing substance having properties to kill undifferentiated epithelial cells.

22. A method of performing cataract surgery on an eye to prevent capsule clouding after the surgery comprising the steps of injecting a substance between an anterior capsule and a natural lens, the substance having properties to kill undifferentiated epithelial cells covered by a layer of cortical debris.

23. A composition for administration between an anterior capsule and a lens comprising a buffer-containing, pH adjusted solution having a pH in a range between approximately 1.0 to below 6.5 or a pH in a range between approximately above 7.5 to 14 a visually apparent amount of a dye and 0.5 to 5.0% by weight of a viscoelastic material.

24. The composition of claim 23 wherein said solution comprises a mixture of water, a buffer and an acid.

25. The composition of claim 24 wherein said acid is HCl.

26. The composition of claim 23 wherein said solution comprises a mixture of water, a buffer and a base.

27. The compositon of claim 26 wherein said base is NaOH.

28. The composition of claim 23 wherein said dye is blue.

29. The composition of claim 23 wherein said visually apparent amount of said dye is 0.1 to 10 ppm.

30. The composition of claim 23 wherein said solution has a pH ranging between 5.8 to 6.2 or between 8.0 to 8.4.

31. The composition of claim 23 wherein the solution comprises 0.05 to 5.0% by weight of a buffer.

32. The composition of claim 31 wherein the buffer comprises a mixture of sodium phosphate monobasic and sodium phosphate dibasic.

33. A composition for administration between an anterior capsule and a lens comprising 0.5 to 5.0% by weight of a viscoelastic material and a cell-killing substance containing a buffer having properties to kill undifferentiated epithelial cells.

34. The composition of claim 33 additionally comprising a dye.

35. A composition for administration into an eye between an anterior capsule and a natural lens comprising a buffer-containing hypotonic solution having a salinity less than 0.9% and having properties to kill undifferentiated epithelial cells, a visually apparent amount of a dye, and 0.5 to 5.0% by weight of a viscoelastic material.

36. The composition of claim 35 wherein said solution has a pH in the range between 4.5 to 9.0.

37. The composition of claim 35 wherein said solution has a pH in the range from between 5.8 to 8.4.

38. The composition of claim 35 wherein said solution has a salinity less than 0.6%.

39. The composition of claim 35 wherein said solution comprises 0.05 to 5.0% by weight of a buffer.

40. The composition of claim 39 wherein said buffer comprises a mixture of sodium phosphate monobasic and sodium phosphate dibasic.

41. A composition for administration between an anterior capsule and a lens comprising an epithelial cell-killing substance and buffering means for breaking down cortical debris between the anterior capsule and the lens to expose epithelial cells to the epithelial cell-killing substance.

* * * * *